US006294189B1

(12) United States Patent
Stang et al.

(10) Patent No.: US 6,294,189 B1
(45) Date of Patent: *Sep. 25, 2001

(54) METHOD OF FORMING DECONTAMINANT FOOD PRODUCT

(75) Inventors: Michael A. Stang, Pikesville; Dudley A. Demarest, Jr., Catonsville, both of MD (US)

(73) Assignee: De Novo, Inc., Pikesville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/065,531

(22) Filed: Apr. 24, 1998

Related U.S. Application Data (63) Continuation-in-part of application No. 08/692,239, filed on Oct. 7, 1996, now Pat. No. 5,795,586.

(51) Int. Cl.[7] ............................. A61K 9/28; A61K 9/68; A61K 47/00
(52) U.S. Cl. ........................ 424/441; 424/439; 424/440
(58) Field of Search .................................. 424/439, 440, 424/441; 514/974, 823

(56) References Cited

U.S. PATENT DOCUMENTS

| 294,687 | 3/1884 | Seibert . |
| 1,052,872 | 2/1913 | Williams . |
| 1,542,006 | 6/1925 | Sauer . |
| 1,741,589 | 12/1929 | Scott et al. . |
| 2,143,088 | 1/1939 | Rockwell . |
| 2,787,579 | 4/1957 | Vander Weel . |
| 3,642,986 | 2/1972 | Welch et al. . |
| 3,917,821 | 11/1975 | Manes . |
| 3,932,661 | 1/1976 | Kaugars . |
| 3,934,007 | 1/1976 | Gussin et al. . |

(List continued on next page.)

OTHER PUBLICATIONS

Boehn et al, Flavored activated charcoal as an antidote, BIOSIS AN 79:235921 abs, 1978.*
Cheng et al; Charcoal flavored ice cream, BIOSIS AN 90:103876, 1989.*
Cheng, M., et al., Vet. Hum. Toxicol., vol. 31, No. 4, Aug. 1989, p. 332.
Boehm, J.J., et al., Aust. J. Pharm. Sci., vol. 7, No. 4, 12/78, pp. 119–121.
Cooney, D.D., et al., Am. J. Hosp. Pharm., vol. 34, pp. 1342–1344.
Shaw, F.V., Ceramic Bulletin, vol. 69, No. 9, 1990, pp. 1484–1489.

*Primary Examiner*—Russell Travers
*Assistant Examiner*—Shengjun Wang
(74) *Attorney, Agent, or Firm*—Rosenberg, Klein & Lee (57) ABSTRACT

A method for manufacturing an antidotal food product containing activated charcoal is provided to combine a binder, a filler composition, water, flavoring and sweetener compositions with an activated charcoal to form wafers having a consistency emulating that of a baked cookie. The activated charcoal (110), binder (112), filler (114), water (116), and flavoring and sweetener compositions (118) are combined in a mixer (210) to form a slurry. The slurry is then processed in a spray dryer (220) to form granules. The granules are combined with a lubricant (122) in a blender (230). The dry mixture from blender (230) is then formed into wafers by a tableting type machine in a compression molding step (240). The wafers formed in the compression molding step (240) are then coated in an anti-dusting coating step (250). A sweet creme filling is applied between pairs of the wafers in a cookie sandwich assembly step (270).

20 Claims, 3 Drawing Sheets

U.S. PATENT DOCUMENTS

| | | |
|---|---|---|
| 4,122,169 | 10/1978 | Geils . |
| 4,162,306 | 7/1979 | Laves . |
| 4,529,583 | 7/1985 | Porter . |
| 4,594,249 | 6/1986 | Procter et al. . |
| 4,760,093 * | 7/1988 | Blank et al. .......................... 514/629 |
| 4,761,284 | 8/1988 | Nishimura . |
| 4,767,789 | 8/1988 | Blank et al. . |
| 4,822,765 | 4/1989 | Nishimura . |
| 4,835,186 | 5/1989 | Reuter et al. . |
| 4,859,476 | 8/1989 | Herting . |
| 4,895,723 | 1/1990 | Amer et al. . |
| 5,482,707 | 1/1996 | Saulson . |
| 5,795,586 * | 8/1998 | Stang et al. .......................... 424/441 |

* cited by examiner

METHOD OF FORMING DECONTAMINANT FOOD PRODUCT

RELATED PATENT APPLICATIONS

This patent application is a Continuation-in-Part application of Ser. No. 08/692,239, filed Aug. 7, 1996, now U.S. Pat. No. 5,795,586.

BACKGROUND OF THE INVENTION

1. Field of the Invention

This invention relates to a method for forming an antidotal food product containing activated charcoal that is administered to poisoning victims for decontamination of various poisonous substances that may have been ingested. In particular, this invention relates to a method of producing an antidotal food product containing activated charcoal that is an orally administered antidotal substance having the visual appearance and physical properties to entice proper oral administration to even young children.

More in particular, this invention is directed to a method for forming an activated charcoal decontaminant food product having an appearance, texture and taste that emulates that of a baked cookie.

Still further, the method of this invention includes the steps of mixing activated charcoal with a filler, a binder and water to form a slurry; spray drying the slurry to form a granular composition; blending the granular composition with a friction reducing composition; and, compressing the blended mixture to form a dry friable wafer. Still more in particular, the method of this invention further includes the step of inserting a sweet creamy filling mixture composition between a pair of wafers to form a cookie sandwich-type food product.

2. Prior Art

Poisonings are the ingestion of toxic substances and have historically been and continue to be a significant problem today. With the ongoing proliferation of an expansive variety of commercially-available household products, access to a plethora of toxic substances in the average home is currently at or near an all-time high. While efforts in recent years, such as conspicuous labeling, tamper-proof sealing campaigns, and limiting the number of tablets in bottles of children's medicines, as well as a concerted informational program, appear to have been successful in preventing dramatic growth in the number of poisoning deaths that occur annually, significant numbers of poisoning incidents continue to occur. An overwhelming percentage of those incidents occur at a residence, and the majority of the victims tend to be young children. In 1993 alone, for instance, there were 1,751,476 human poisoning cases reported to recognized Poison Centers, over 90% of which occurred at a residence, according to the 1993 *Annual Report of the American Association of Poison Control Centers Toxic Exposure Surveillance System*. Children under the age of six made up approximately 56% of the victims in those cases. Considering that at that time only about 70% of the American population actually had access to a Poison Center recognized in the study, the number of incidents that actually occurred in 1993 is likely to have been significantly higher than these numbers would indicate, with the total number of cases more realistically been on the order of 2,500,000.

In the emergency treatment of poisoning victims, the effort centers around two main objectives: general support and stabilization of the victim, and decontamination of the victim. As decontamination and treatment must begin immediately in such toxicological emergencies, often without the benefit of full and thorough clinical information on the patient, it is particularly important that any drug or therapeutic substance administered to the patient be substantially free of unwanted side effects that may cause unforeseen complications, or even death. For this reason, sorbents which, when introduced into the patient's gastro-intestinal tract, resist decomposition and adsorb the ingested toxins until eventual excretion by the patient, have been employed for decontamination. Of those sorbents, activated charcoal has emerged in the field of emergency toxicological treatment as the decontaminant of choice. Its routine use in the treatment of poison victims did not become widespread until the 1980's. However, its administration to poisoning victims has now surpassed the administration of syrup of ipecac as the single most important general toxicological treatment measure.

Activated charcoal is a fine, black, powdery substance which is tasteless, odorless, and non-toxic. Activated charcoal is generally formed by oxidation (activation) of combustion residue derived from a controlled combustion process performed on wood, peat, or other organic material. The oxidation and controlled combustion steps combine to yield a substance composed of extremely porous particles which give it extraordinarily high internal surface area, typically ranging between 900 $m^2/g$ and 2400 $m^2/g$. Due to its extraordinary surface area, activated charcoal exhibits great adsorptivity and, thus, has proven to be quite effective as a decontaminant when introduced in sufficient quantities into the gastro-intestinal tract of a poisoning victim. The highly adsorptive activated carbon particles within the gastro-intestinal tract are capable of adsorbing toxin, not only from the contents of the gastro-intestinal tract but even from the bloodstream (by "intestinal dialysis"), from the blood vessels which supply the gastro-intestinal tract. Those toxins become bound to the activated charcoal, and are then excreted in the stool.

Activated charcoal is currently available in several forms to be orally administered to poisoning victims. In the most widely used form, activated charcoal is contained in a suspension such as the commercially available ACTIDOSE AQUA and CHARCOAID 2000 suspensions. Activated charcoal is also available extensively in Europe, and to a more limited extent in the United States, simply in its powdered or granulated form for mixture within a drinkable liquid prior to ingestion. In yet another form, activated charcoal is contained in over-the-counter tablets or capsules widely available in Europe for the treatment of gas and upset stomach. Use of these tablets or capsules for decontamination in toxicological treatment, however, is not readily feasible. Even if all the active ingredients other than activated charcoal were removed therefrom, the relatively high dosages required in most poisoning incidents would necessitate the ingestion of many such tablets or capsules, a daunting task even for the average adult, let alone for the average young child.

In whatever form activated charcoal is delivered to the gastro-intestinal tract, suspended in a liquid, compressed within a tablet or capsule, or simply in its raw powdery state, the activated charcoal is likely to have significantly beneficial, if not life-saving, effects on the poisoning victim, if it can be properly delivered in the necessary dosage to the gastro-intestinal tract of the victim. Therein lies the single greatest obstacle to optimal utilization of activated charcoal as a decontaminant in toxicological treatment. Each of the currently available forms in which activated charcoal is available for oral ingestion utterly fails to adequately induce or at least encourage proper ingestion of a significant dose of the activated charcoal by the victim. Essentially, except for the tablet or capsule form (which presents its own obstacles to ingestion), the antidotal substances are extremely unpalatable and, quite noxious. Liquid antidotal suspensions containing activated charcoal, for instance, form a black gritty liquid bearing a striking resemblance to old engine crank case oil and lacks the pleasant taste which, theoretically, might cause the ingesting individual to even momentarily forget the unpleasant appearance, texture, and consistency of that which he or she is ingesting.

Whereas to a mature adult poisoning victim, the noxiousness of an activated charcoal-containing antidote may simply represent a trivial, though unpleasant, consequence that must be tolerated to avoid the far greater consequences of his or her serious predicament, it would hardly be such a trivial matter to a young child victim. To that young child or any other victim lacking the mental or emotional capacity to fully appreciate the magnitude of the situation and therefore incapable of seeing beyond the overbearing experience of ingesting the given antidote, the palatability of the antidote, both in appearance and taste, will not only determine how pleasant the ingestion experience is, but will actually determine whether or not the ingestion occurs in the first place. That might, in part, explain why with 1,751,476 reported poisoning incidents in 1993, activated charcoal was administered in that year to only 127,857 victims, despite the fact that the relatively risk-free benefits of activated charcoal in toxicological treatment had been widely recognized by emergency care providers since well before 1993. Children, especially very young children, who represent the class of individuals most vulnerable to accidental poisonings and who, in fact, make up the majority of the victims in poisoning incidents, are loathe to ingest activated charcoal in the various forms in which it may currently be presented to them.

This fact is borne out by empirical studies performed on the subject, and by the first-hand experiences of seasoned emergency health care professionals. For instance, in a 1987 study, Grbcich, et al., "Administration of Charcoal in the Home", *Vet. Hum. Toxicology*, 29, 458 (1987), the authors studied the cases of six children between the ages of one and five years who were given a liquid suspension containing 1 g/kg of activated charcoal after they had accidentally ingested a toxic substance in amounts that did not necessitate hospital treatment. Of those children, none ingested the full amount of the suspension given to him or her, and only one ingested as much as half of the amount given. The authors observed that "All parents had considerable difficulty getting the child to drink the charcoal [suspension] and most indicated they would not choose this method of oral decontamination in the event of a future poisoning." The experiences in the emergency room have been, by and large, no different from the experiences of these parents. Most health care providers currently consider themselves extremely fortunate if they are able to coax, trick, or otherwise prompt a young child poisoning victim to ingest any amount of an activated charcoal antidote.

Faced with this obstacle, forced ingestion is not a viable option. Aside from its moral and legal implications, forced ingestion would pose a substantial collateral health risk. The direct health risks of activated charcoal therapy are nominal, if any, but one indirect risk, the serious occurrence of which has been reported in a few cases, is that of activated charcoal aspiration by the victim. While the risk of aspiration accompanies any oral ingestion of a substance, that risk is greatly amplified where ingestion of the substance is imposed upon a non-cooperative child who is instinctively resisting that ingestion. The risk becomes even greater when the ingestion is being forced by the child's parent, guardian, or any other individual having a personal relationship with the child, who might himself or herself understandably be in an excited, agitated, or even bewildered state given the exigencies surrounding a typical poisoning incident.

In cases where activated charcoal must be administered to an uncooperative patient, there is no choice but to introduce it through a nasogastric or orogastric tube. This procedure often requires physically restraining the patient. It also carries the risk of trauma to the mouth, pharynx, esophagus and stomach. Inadvertent placement into the tracheobronchial tree can result not only in trauma to these areas, but in massive charcoal aspiration which can be fatal.

Efforts have been made to render the currently available forms of activated charcoal more palatable, but those efforts have at best yielded only products that may be somewhat less noxious, but certainly not palatable, especially to young children. Still further, those efforts at times have led to the introduction of substances or components which may actually diminish the adsorptivity of the activated charcoal, thereby undermining the singular central function of the antidote.

What is currently needed, therefore, is an antidotal product containing ample quantities of activated charcoal which is palatable to young children and in which the adsorptivity of the activated charcoal is not diminished in any substantial measure. It is absolutely essential that the antidotal product not only be palatable enough to entice the average young child to place it into his or her mouth, but that the product also be palatable enough to encourage the child to willingly ingest adequate quantities thereof.

The method of the instant invention produces an antidotal food product containing activated charcoal which uniquely provides the necessary palatability not heretofore seen in prior art antidotes. The combination of particular binders, fillers, flavorings and sweeteners, in particular relative quantities and combined into a liquid slurry which is then processed in a spray dryer provides granules which when compressed together form a cookie-like wafer which has a consistency emulating that of a baked cookie. By virtue of the spray drying process step, each particulate is a combination of the multiple ingredients so that the filler, binder, flavoring and sweeteners are combined with the activated charcoal in each minute particulate of the wafer. To further add to the appeal and sweet flavor of the antidotal food product, such is manufactured in the form of a readily recognizable cookie sandwich having a pair of black wafers sandwiching a creamy filling. The subject antidotal food product in this form has the appearance, weight and feel of very common and popular cookie treats. To the average young child, the subject antidotal food product is, thus, indistinguishable from the delectable cookie treats he or she is accustomed to eating. In such a form, pharmacologically significant quantities of activated charcoal are readily ingested by young poisoning victims.

By virtue of the spray drying process, the binder is deposited on the external surface of the resulting granules, thereby promoting binder-to-binder contact during compaction in the compression molding step. As a result, a lower percentage of binder can be utilized to form the wafers, thereby enhancing the crumbly, cookie-like, texture of the finished wafers. Thus, a child would not only be enticed to place the subject antidotal food product into his or her mouth, he or she would actually be encouraged thereafter to chew and swallow the product, as such closely emulates the baked cookie treat the child is so familiar with. The pleasant taste further encourages the child to likewise ingest addition "activated charcoal cookies" which make up the required pharmacological activated charcoal dosage.

An important factor in the proper use of activated charcoal or any other decontaminant in toxicological treatment is, in addition to its ingestion in significant does by the victim, the promptness with which the ingestion occurs. Ideally, the activated charcoal ought to be administered at the site at which the poisoning incident occurs (which in most cases is the victim's home) immediately following the discovery of the accidental ingestion, before the ingested toxins have had the opportunity to be extensively absorbed into the bloodstream. Yet, most likely due to the difficulty of administering currently available activated charcoal antidotes, arising from their unpalatability, those antidotes are almost exclusively administered in medical institutions. Thus, many precious minutes, if not hours, after the accidental toxic ingestion has occurred, the victim is brought to the medical institution for treatment. In contrast, the antidotal food product formed by the inventive method, given its inherent palatability, could easily be administered in the home or any other setting outside a medical institution, and by any individual. Hence, the antidotal food product formed by the instant inventive method would not only expand the usage of activated charcoal as a decontaminant, but it would actually enhance, in a significant manner, the effectiveness of that usage.

The realization of a method for forming an antidotal food product which has a texture and taste which emulates that of a baked cookie product has been no trivial task. The development of the antidotal food product and the method for making such a product has required extensive testing and research. The inventive method described herein is a result of that extensive testing and research which has been carried out over a number of years.

SUMMARY OF THE INVENTION

A method of forming a toxin decontaminant food product for ingestion into the gastro-intestinal tract of a user is provided. The method includes the step of mixing a first predetermined weight of a sorbent particulate composition having a predetermined adsorption value with respect to a toxin with a second predetermined weight of a substantially non-interfering filler, a binding composition and water to form a slurry. The slurry is next processed in a spray dryer to form a granular composition. The granular composition is blended with a friction reducing composition in a next step. Then, the blended mixture is compressed to form a dry friable wafer having a consistency emulating that of a baked cookie.

DESCRIPTION OF THE PREFERRED EMBODIMENT

A great problem exists in the treatment of small children for the ingestion of toxic substances. While it is well known that activated charcoal is pharmacologically effective for treating the ingestion of toxins, its consistency, color and taste are not well tolerated by children. To overcome this problem, a method is described for combining a sorbent particulate composition with a binder, filler and flavoring compositions to form a wafer with a consistency emulating that of a baked cookie. By the method described in following paragraphs, wafers containing the sorbent particulate composition are formed which have a crumbly cookie-like texture. A flavored filling is inserted between a pair of wafers to emulate the look and taste of popular cookie products commercially sold and easily identified by young children, to entice them to eat the antidotal food product formed by the instant method.

Each wafer formed by the instant method includes activated charcoal having a weight percentage within the approximating range of 40%–70%, a binder having a weight percentage within the approximating range of 2%–10%, and fillers, sweeteners and flavoring agents having a combined weight percentage within the approximating range of 25%–50%. When the wafer constituents are combined in accordance with the method shown in the block diagram of FIG. 1, disk-shaped black wafers are formed. The wafers exhibit a compressed granular texture and a degree of friability akin to that of a class of cookie treats that are quite popular with children. The degree of friability is such that the wafers are easily crumbled by the average biting force generated by even a very young child. The degree of friability is also such that the crumbled wafers may thereafter be effectively disintegrated by the subsequent chewing action generated by the young child.

The wafers produced by the instant method exhibit a degree of rich, sweet flavor to accompany their cookie-like crumbly texture. It is important that the sweet flavor of the wafers be sufficient to encourage substantial chewing prior to swallowing.

To enhance both the sweet flavor of the wafers, and to enhance the emulation of the readily identifiable class of cookie treats, a creamy white filling is sandwiched between a pair of wafers. The precise consistency, color and taste of the filling is not important to the invention, however, it is desired that the filling be of a consistency similar to that found in commonly-consumed cookie sandwich treats. Thus, the color and texture of the filling should resemble that of the commonly-consumed cookie sandwich treat, and its flavor should be sufficiently sweet so as to supplement or augment the sweet flavor of the wafers themselves. One filling formulation which meets the above stated requirements is formed by powdered sugar in an approximating weight percentage of 71.97%, melted icing shortening in an approximating weight percentage of 14.75%, lecithin in an approximating weight percentage of 0.05%, high fructose corn syrup in an approximating weight percentage of 12.68%, vanilla flavor in an approximating weight percentage of 0.32%, and salt in an approximating weight percentage of 0.23%. Those ingredients are combined and mixed to form a uniform creamy paste.

The preferred sorbent composition is an activated charcoal. Activated charcoal is a black, powdery substance characterized by an extraordinary porosity which gives its particulates a high internal surface area. A medicinal grade of this activated charcoal is commercially available from a limited number of manufacturers worldwide, and in forms respectively exhibiting various levels of internal surface area, up to approximately 2400 $m^2/g$. Although any medicinal activated charcoal may be used to form the wafers by the instant method, an activated charcoal having an internal surface area at the higher end of the range is preferred. The higher the internal surface area of the activated charcoal utilized, the lower the quantity of activated charcoal required to be administered for a given quantity of toxin.

Lab tests verify that activated charcoal of greater surface area exhibits greater adsorptivity per unit gram thereof. To the extent possible, therefore, it is preferable that the activated charcoal of maximum surface area be incorporated into the subject wafers. This not only tends to decrease the minimum weight percentage of activated charcoal necessary in each wafer, thereby enabling the incorporation in greater proportional quantities of the other flavor-enhancing compositions, and also reducing the number of wafers which must be ingested for decontamination of a given quantity of ingested toxin.

With respect to the other compositions that are combined with the activated charcoal, several factors are of paramount importance in their selection. First the accompanying compositions must provide for the otherwise tasteless, gritty activated charcoal, a friable, yet chewable crumbly texture and a pleasant degree of sweet flavor, to emulate a sweet cookie treat. The compositions combined with the activated charcoal must provide those attributes without substantially interfering with the adsorptivity of the activated charcoal. The component compositions, previously discussed, when combined in the proportional quantities indicated, have been found to reduce the overall adsorptivity of the activated charcoal in its pure form by approximately 6%. That degree of reduction has been determined to be an acceptable trade-off given the exceptional flavor, texture and friability level attained in the wafer. Through the use of an activated charcoal having an internal surface area approximating 2400 $m^2/g$, such more than compensates for the small reduction in overall adsorptivity of the wafer versus the activated charcoal in its pure form when compared to the activated charcoal decontaminant products currently on the market.

The component compositions of the filling composition, as previously discussed, are important in that they combine in the indicated proportions to form a sweet, creamy filling which complements the dry, somewhat diluted sweetness of the wafers. The sweet, creamy filling tends to promote the chewing of the wafers for a longer period of time. The increased chewing time is important to promoting the dispersal of the activated charcoal. Kinetics tests performed with various wafer prototypes have indicated that greater dispersement of the activated charcoal effects measurably faster rates of toxin adsorption.

Observations from numerous other tests indicate that the component compositions of the filling present no significant threat to adsorptivity of the activated charcoal contained in the wafers. Accordingly, the choice of component compositions and their respective weight percentages are important to the present invention to the extent that they affect the consistency, color and taste of the resulting filling, which characteristics are important to the palatability of the end product. No matter how adsorptive of a sorbent composition is provided, if a child will not consume it, no pharmacological benefit will be realized. The particular choice of component compositions and their corresponding weight percentages are therefore determined primarily by those considerations. The component compositions, previously discussed, are, with the exception of the shortening in the filling, each devoid of a fat component, a feature desirable in light of interference tests. Interference tests for various component compositions have indicated that fat-containing compositions observably interfere with the activated charcoal contained in the wafers.

Figure 1:
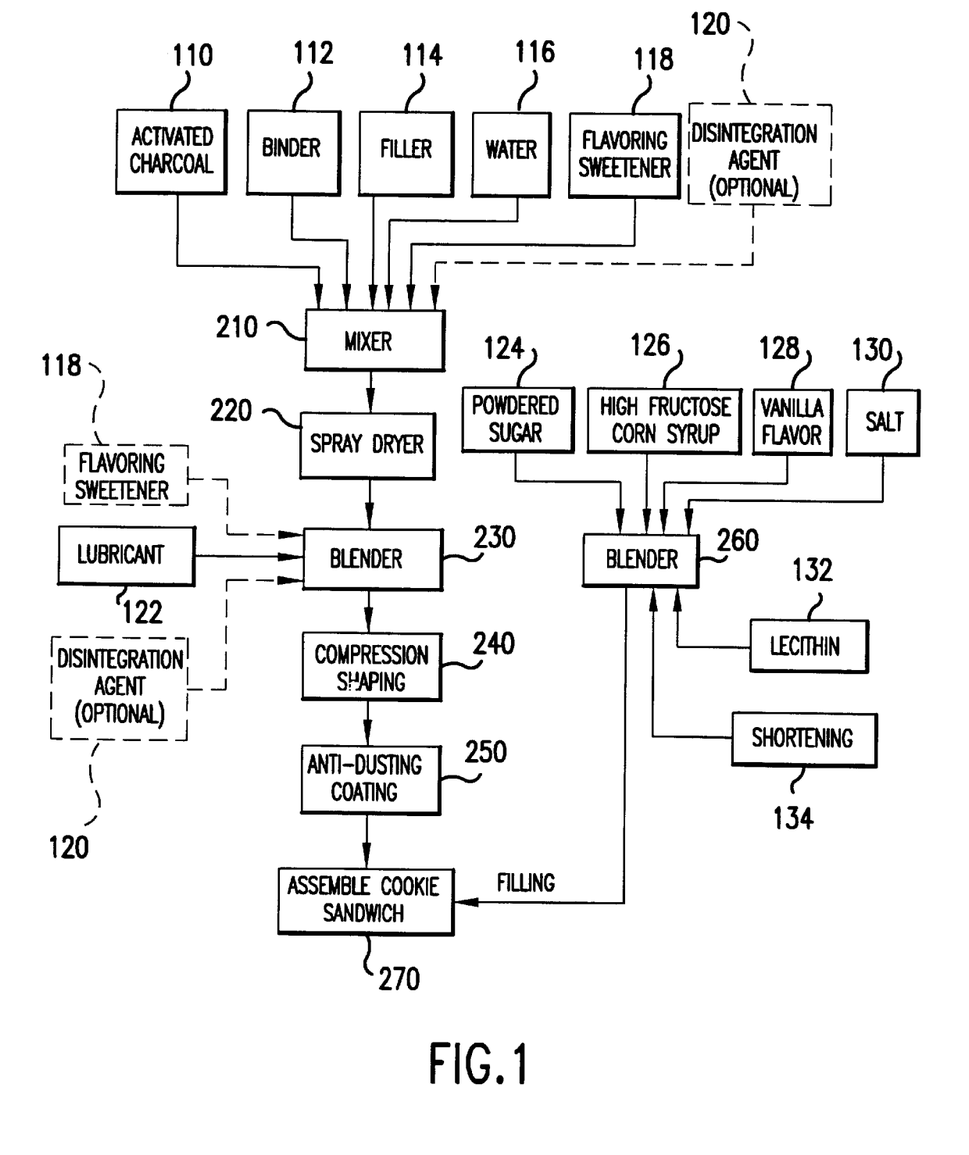
FIG. 1 block diagram illustrating the sequence of steps in the inventive method of forming the toxin decontaminant food product.

The method for forming the decontaminant food product is shown in FIG. 1. Appropriate quantities of the base wafer ingredients, in the appropriate weight percentage ranges discussed, are added to a mixer 210. The activated charcoal 110, binder 112, filler 114 and water 116 are combined to form a slurry in the mixer 210. The flavoring and sweetener 118 and an optional disintegration agent 120 may also be added to the slurry in mixer 210, or alternately added in a subsequent processing step, as will be discussed in following paragraphs. The binder may be povidone (PVP), hydroxypropyl methylcellulose, or other fat-free binder compositions known in the food and pharmaceutical arts. The filler 114 may be a lactose composition, some other sugar, such as sucrose, or any one of a number of starches. The flavoring and sweetener 118 may comprise a chocolate creme flavor, either alone or combined with a vanilla dry flavor as well as aspartame or a natural sugar and salt. A disintegration agent may be incorporated into the wafers made by the method of FIG. 1. The disintegration agent serves to wick moisture to the interior of the wafer or swells in the presence of moisture to facilitate the breaking up of the wafer during its consumption. Disintegrants and super-disintegrants are well known in the pharmaceutical arts and include the commercially available disintegrant, AC-DI-SOL (A trademark owned by FMC Corp. of Philadelphia, Pa.), starches, modified starches, modified polymers, and the like. Sufficient water 116 is added so that the output from mixer 210 is a well homogenized slurry. The slurry is fed to the spray dryer 220.

Spray dryer 220 may be any one of a number of commercially available spray dryer systems available from such manufacturers as NIRO ATOMIZER, INC. of Columbia, Md. Spray dryer 220 atomizes the slurry into fine droplets, with each droplet containing numerous finely divided solid particles. The cloud of droplets produced within the spray dryer is then contacted with a stream of hot gas, such as air. During the contact time with the heated air, the water in the slurry evaporates from the droplets, leaving the dry solids behind in the form of granules containing a respective distribution of the slurry constituents, less the water. Evaporation is immediate and rapid from the surface of the droplets, with soluble materials being left behind to form a skin or film on the surface of the droplet. A single particulate is derived from each droplet subsequent to evaporation of all of the droplet's water content. For the decontaminant composition, the particulates have a mean particle size which may be within the approximate range of 10–300 micrometers, with a spherical shape, depending upon the method of atomizing the slurry. The binder 112 ends up for the most part on the outside of the particulates, on the outside surface of the filler and active ingredient. Thus, when the particulates are compressed, it is believed that binder-to-binder contact is achieved to better hold the wafer structure together. By virtue of the binder-to-binder contact, less overall binder is required to maintain the wafer's form, allowing a greater percentage of the other constituents to be incorporated in each wafer. That arrangement also contributes to the resulting baked cookielike texture of the wafers.

The particulates, or granules obtained from spray dryer 220 are next transferred to blender 230. A lubricant 122, such as magnesium stearate is added to blender 230 to be mixed with the granules from spray dryer 220. The blended composition is then formed into a wafer in the compression shaping operation 240. The wafers may be formed utilizing a tableting machine, of the type well known in the pharmaceutical industry. The lubricant 122 which was combined with the granules in the blender 230 allows the wafers to be easily removed from the die in which they are formed. Compressive forces in the approximating range of 600 kg–2000 kg is applied to the blended granules in the tableting machine to form the wafers.

The compression or tableting molding process 240 provides the decontaminant food product in the form of a wafer. The wafers supplied from the compression process 240 to a coating step 250 where the wafers are then coated with an anti-dusting film. The anti-dusting film is a sugar film formed of sucrose or dextrose, or some like composition, to form an encapsulation around the activated charcoal particulates to minimize smearing of the activated charcoal when the wafer is grasped by a user. Such coating operations are usually carried out on a perforate conveyor belt where a spray coating section is followed by a drying section.

The filling is prepared by mixing and evenly blending, in blender 260, appropriate quantities of powdered sugar 124, high fructose corn syrup 126, vanilla flavor 128, salt 130, lecithin 132, and shortening 134. An appropriate quantity of the resulting creamy mixture supplied from blender 260 is placed between a pair of wafers delivered from the anti-dusting coating process 250 to assemble a cookie sandwich decontaminant food product at step 270. The assembly step 270 is carried out by a commercially available sandwiching machine, well known in the confection art.

Instead of mixing the flavoring and sweetener 118 with the other constituents in the mixer 210, such can be added with the lubricant 122 to the blender 230 to be mixed with the granules from the spray dryer 220. Likewise, if the optional disintegration agent 120 is to be employed, such may also be added with the lubricant 122 to the blender 230. The flavoring and sweetener 118 and the disintegration agent 120 may both be combined with the lubricant 122 in the blender 230, or either one alone, with the other being combined in mixer 210, as previously described.

With regard to the tests performed for the subject decontaminant food product, a large sampling of prototypes developed in the inventive process were tested to ensure that the decontaminant food product overcame the shortcomings of the prior art. Comparative kinetics tests to determine the rate at which a given prototype adsorbed a toxin, and equilibrium adsorption tests to determine the adsorption capacity of the given prototype were performed. Interference tests were also performed to determine the degree by which each component composition tended to diminish the adsorptivity of the activated charcoal, when processed in accordance with the inventive method, were performed for each prototype. Still further, the taste and texture of each prototype was assessed.

All tests were conducted in vitro by mixing a predetermined amount of a test substance into a stock solution. The in vitro stock solution used in each test consisted of 1 g/L of sodium salicylate dissolved in a simulated gastric fluid solution containing 2.0 g/L of NaCl, 7.0 mL/L of 12 N strength concentrated Hcl, and distilled water. The simulated gastric fluid was characterized in this form by a pH level of 1.2, the salicylate of this pH level being more than 99.99% in the form of undissociated salicylic acid, which is very similar in its properties to aspirin, or acetylsalicylic acid.

Equilibrium adsorption tests for determining the total amount of salicylate that a given test substance may potentially adsorb, if allowed to attain equilibrium conditions, was conducted with the following procedures. First, a predetermined amount of the substance to be tested was placed in a glass vial, and 20 mL of the stock solution was added to that vial. The vial was thereafter continuously shaken by placement on a shaking table for approximately 15 hours. This caused the test substance to fully disintegrate such that the activated charcoal contained therein attained virtually perfect adsorption equilibrium with the salicylate in the stock solution.

The kinetics tests were conducted generally by performing the following steps. Approximately 500 mL of the stock solution was poured into a 1 liter glass container. A predetermined quantity of the given test substance was then introduced into the solution in the glass container. The container was then placed on a shaking table and shaken thereby at a 60 cycles per minute oscillation frequency. Samples were taken at various times. Activated charcoal was filtered from each sample and the solution analyzed calorimetrically to determine the salicylic concentration corresponding to the given sample time.

Figure 2:
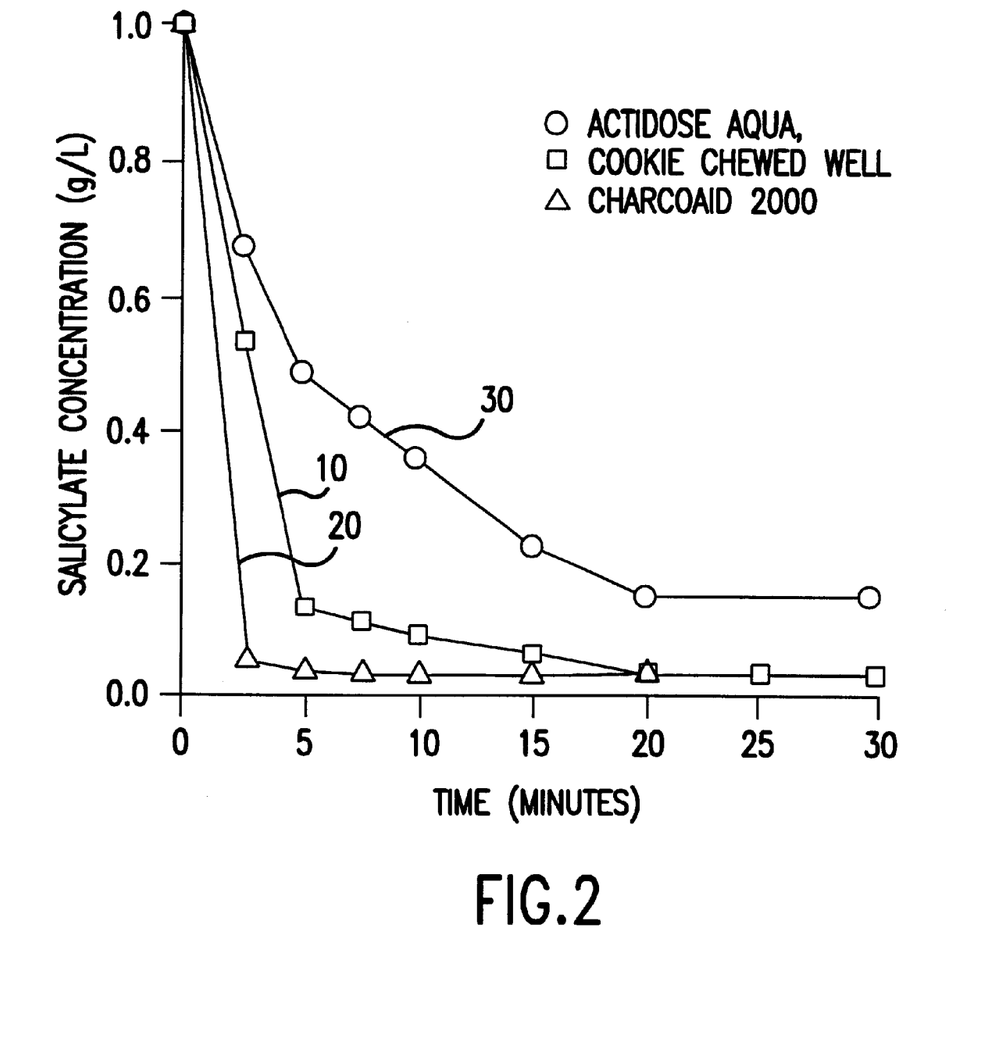
FIG. 2 graphical representation of adsorption kinetics test data for the toxin decontaminant food product made in accordance with the present invention; and, FIG. 3 graphical representation of equilibrium adsorption test data for the toxin decontaminant food product made in accordance with the present invention.

Comparative kinetics test results for a cookie product formed by sandwiching a pair of wafers manufactured by the inventive process, as previously described, is shown in FIG. 2. For this test, a cookie weighing approximately 6.80 grams (5.15 g wafers and 1.65 g filling) was chewed vigorously by the individual conducting the test, then introduced into a given volume of the stock solution. The decontaminant cookie was compared with two commercially available activated charcoal liquid suspensions. As shown by curve 10, the concentration of salicylate in the solution decreased from 1.0 g/L to well under 0.2 g/L within 5 minutes after the cookie's introduction into the solution. After this very rapid initial decrease, the rate of salicylate concentration decreases more gradually until equilibrium conditions are reached.

The superior adsorption performance of the subject decontaminant food product made in accordance with the inventive method is apparent when curve 10 is compared with curve 30, plotting the decrease in salicylate concentration upon introduction therein of 10.06 ml. of ACTIDOSE AQUA, a liquid suspension commercially marketed by PADDOCK LABS, INC., Minneapolis, Minn. That amount of ACTIDOSE AQUA was determined to contain approximately the equivalent amount of activated charcoal as contained in the cookie sample from which curve 10 was derived. Comparison of the two curves indicates that the cookie formed by the instant inventive method not only reduced the salicylate concentration in the simulated gastric fluid solution at a significantly faster rate, but also yielded a significantly greater overall reduction in the concentration than a comparable amount of ACTIDOSE AQUA suspension. For instance, the salicylate concentration, 5 minutes subsequent to introduction of the subject cookie, was substantially below 0.2 g/L. Whereas, the salicylate concentration 5 minutes subsequent to introduction of the ACTIDOSE AQUA was observed to be approximately 0.5 g/L. After 30 minutes, the salicylate concentration had diminished to approximately 0.03 g/L with the subject cookie, whereas it had begun to level off at approximately 0.15 g/L with ACTIDOSE AQUA.

In another comparative analysis, a relatively new product CHARCOAID 2000, is marketed by REQUA, INC. of Greenwich, Conn. 8.43 ml. of CHARCOAID 2000, containing approximately the equivalent amount of activated charcoal as contained in the subject cookie sample, was added to the simulated gastric fluid solution and the salicylate concentration sampled as in the previous experiments, with the adsorption performance being indicated by curve 20. It is seen that the liquid suspension CHARCOAID 2000 closely approaches its peak adsorption in approximately 2½ minutes, with the change in adsorption being very flat from that point on. While the initial slope of the change in adsorption for the subject cookie is not as steep as that of the CHARCOAID 2000 suspension, it does compare very favorably therewith. For the treatment of ingestion of toxins by children, the increased rate of adsorption by the CHARCOAID 2000 product is for naught, as children will not ingest a sufficient quantity of the decontaminant fluid due to its color, texture and taste.

Figure 3:
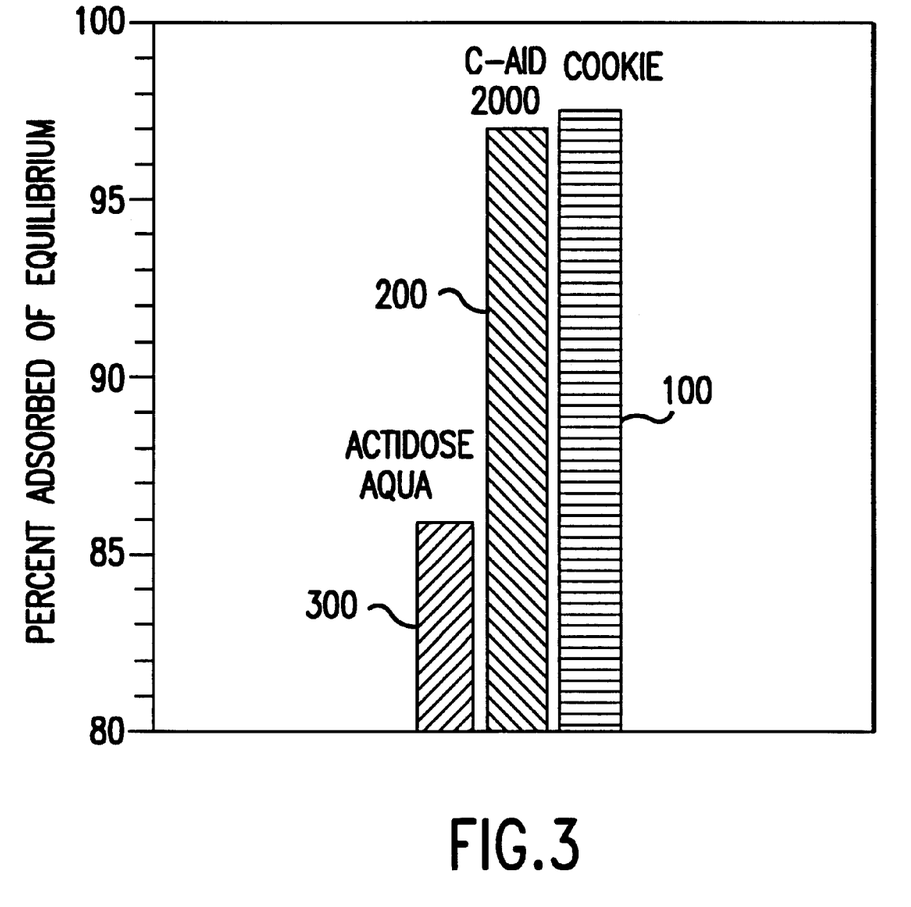

When taken to equilibrium, as shown in FIG. 3, the adsorption of the subject cookie, shown by bar 100, reached approximately 97.4%, whereas the CHARCOAID 2000 reached 97%, as indicated by the bar 200. The ACTIDOSE AQUA reached an adsorption of approximately 85.8%, as indicated by the bar 300. Those results are consistent with the difference in internal surface area of the activated charcoal utilized in the respective products.

The pleasant flavor introduced into each wafer by the additional component compositions not only encourage thorough and complete chewing which enhances the adsorption kinetics by dispersing the activated charcoal contained in the wafer, but also has a more direct effect on charcoal dispersion. The pleasant flavor induces the user's salivary glands to produce more saliva than it would otherwise produce in the absence of such a pleasant flavor. The additional saliva, in turn, serves as a vehicle for more efficient dispersion of the charcoal particles. The filling composition offers a concentrated sugary flavor which supplements and augments the flavor of the wafers. Often, however, consumed cookie sandwich treats are consumed in parts by children who first disassemble the sandwich by separating at least one wafer from the filling, then proceed to consume the separated parts in sequence rather than in toto. It is, therefore, important that the wafers in and of themselves exhibit a sweet and pleasant flavor so that they are desirable to the average young child's palate, separate and apart from any filling composition. The flavor of the wafers is enhanced by the inventive method for their manufacture. By forming a slurry of substantially all the wafer (cookie) constituents and then performing a spray drying operation to form granules, each granule defines a substantially homogenous mixture of the wafer components which are then subsequently compressed into the wafer form. Thus, each minute granule contains the components which define the flavor, texture and active ingredient of the decontaminant food product, thereby avoiding any change in flavor as the product is chewed by a user. The formation of the binder on the outer surface of each granule allows a smaller quantity of binder to be used to maintain the compacted constituents in the wafer form, and contributes to the achievement of the desired baked cookie-like texture.

Although this invention has been described in connection with specific forms and embodiments thereof, it will be appreciated that various modifications other than those discussed above may be resorted to without departing from the spirit or scope of the invention. For example, equivalent method steps may be substituted for those specifically shown and described, certain combinations of method steps may be used independently of others, and in certain cases, the sequence of method steps may be reversed or interposed, all without departing from the spirit or scope of the invention as defined in the appended claims.

What is claimed is:

1. A method of forming a toxin decontaminant food product for ingestion into the gastro-intestinal tract of a user comprising the steps of:
    (a) mixing a plurality of component materials including a first predetermined weight of a sorbent particulate composition having a predetermined adsorption value with respect to a toxin, said sorbent particulate composition including activated charcoal, a second predetermined weight of a non-adsorbent interfering filler, a binding composition, and water to form a slurry;
    (b) spray drying said slurry to form a granular composition including a plurality of granules each defining a homogenized mixture of said component materials;
    (c) blending said granular composition with a friction reducing composition; and,
    (d) forming a dry friable wafer having a homogeneous flavor and a consistency emulating that of a baked cookie, said forming step including compressing said blended mixture with a predetermined compressive force.

2. The method for forming a toxin decontaminant food product as recited in claim 1 wherein said activated charcoal is characterized by an internal surface area approximating at least 2,000 $m^2/g$.

3. The method for forming a toxin decontaminant food product as recited in claim 2 wherein said slurry includes said activated charcoal in the approximating weight range of 40% to 70% thereof.

4. The method of forming a toxin decontaminant food product as recited in claim 1 wherein said filler includes a sugar in the approximating weight range of 25% to 50% of said slurry.

5. The method of forming a toxin decontaminant food product as recited in claim 1 wherein said filler includes a starch in the approximating weight range of 25% to 50% of said slurry.

6. The method of forming a toxin decontaminant food product as recited in claim 1 wherein said binding composition includes a povidone composition in the approximating weight range of 0.2% to 10% of said slurry.

7. The method of forming a toxin decontaminant food product as recited in claim 1 wherein said binding composition includes a hydroxypropyl methylcellulose composition in the approximating weight range of 0.2% to 10% of said slurry.

8. The method of forming a toxin decontaminant food product as recited in claim 1 wherein said step of mixing includes the step of additionally adding a release agent with said sorbent particulate composition.

9. The method of forming a toxin decontaminant food product as recited in claim 1 wherein said step of compressing is followed by the step coating said dry friable wafer with an anti-dusting film.

10. The method for forming a toxin decontaminant food product as recited in claim 1 further including the steps of:
    (a) forming at least a pair of said dry friable wafers;
    (b) blending together predetermined weights of a powdered sugar composition, a high fructose corn syrup composition, a vanilla flavor composition, and a salt composition to form a filling mixture composition; and,
    (c) sandwiching said filling mixture composition between said pair of dry friable wafers.

11. A method of forming a toxin decontaminant food product for ingestion into the gastro-intestinal tract of a user comprising the steps of:
    (a) mixing a plurality of component materials including a first predetermined weight of a sorbent particulate composition comprising activated charcoal having a predetermined adsorption value with respect to a toxin, a second predetermined weight of a non-absorption interfering filler, a binding composition, and water to form a slurry;

(b) spray drying said slurry to form a granular composition including a plurality of granules each defining a homogenized mixture of said component materials;

(c) blending said granular composition with a flavoring composition;

(d) compressing said blended mixture to form at least a pair of dry friable wafers, each said wafer having a homogeneous flavor and a consistency emulating that of a baked cookie;

(e) blending together predetermined weights of a powdered sugar composition, a high fructose corn syrup composition, a vanilla flavor composition, and a salt composition to form a filling mixture composition; and, (f) sandwiching said filling mixture composition between said pair of dry friable wafers.

12. The method for forming a toxin decontaminant food product as recited in claim 11 wherein said slurry includes said activated charcoal in the approximating weight range of 20% to 60% thereof.

13. The method of forming a toxin decontaminant food product as recited in claim 11 wherein said filler includes a sugar in the approximating weight range of 25% to 50% of said slurry.

14. The method of forming a toxin decontaminant food product as recited in claim 11 wherein said filler includes a starch in the approximating weight range of 25% to 50% of said slurry.

15. The method of forming a toxin decontaminant food product as recited in claim 11 wherein said binding composition includes a povidone composition in the approximating weight range of 0.2% to 10% of said slurry.

16. The method of forming a toxin decontaminant food product as recited in claim 11 wherein said binding composition includes a hydroxypropyl methylcellulose composition in the approximating weight range of 0.2% to 10% of said slurry.

17. The method of forming a toxin decontaminant food product as recited in claim 11 wherein said step of mixing includes the step of additionally adding a release agent with said sorbent particulate composition.

18. The method of forming a toxin decontaminant food product as recited in claim 11 wherein said step of blending includes the step of additionally adding a release agent with said granular composition.

19. The method of forming a toxin decontaminant food product as recited in claim 11 wherein said step of compressing is followed by the step coating each said dry friable wafer with an anti-dusting film.

20. A method of forming a toxin decontaminant food product for ingestion into the gastro-intestinal tract of a user consisting substantially of the step of forming a sorbent particulate composition into a dry friable wafer with a homogeneous flavor and a consistency emulating that of a baked cookie, said step of forming comprising:

(a) mixing a plurality of component materials including a first predetermined weight of a said sorbent particulate composition having a predetermined adsorption value with respect to a toxin, said sorbent particulate composition including activated charcoal, a second predetermined weight of a substantially non-adsorbent interfering filler, a binding composition, and water to form a slurry;

(b) spray drying said slurry to form a granular composition including a plurality of granules each defining a homogenized mixture of said component materials;

(c) blending said granular composition with a friction reducing composition; and, (d) compressing said blended mixture at a predetermined compressive force.

* * * * *

UNITED STATES PATENT AND TRADEMARK OFFICE
CERTIFICATE OF CORRECTION

PATENT NO.         : 6,294,189 B1                                          Page 1 of 1
APPLICATION NO. : 09/065531
DATED              : September 25, 2001
INVENTOR(S)       : Michael A. Stang et al.

It is certified that error appears in the above-identified patent and that said Letters Patent is hereby corrected as shown below:

On the title page, in Related U.S. Application Data (item 63):

Please correct the filing date of application No. 08/692,239 from "Oct. 7, 1996" to --Aug. 7, 1996--.

Signed and Sealed this

Twenty-second Day of May, 2007

JON W. DUDAS
*Director of the United States Patent and Trademark Office*